(12) United States Patent
Bauer et al.

(10) Patent No.: US 7,651,290 B2
(45) Date of Patent: Jan. 26, 2010

(54) DEVICE WITH PULL TAB ACTIVATION

(75) Inventors: Walter G. Bauer, Neenah, WI (US); Tammy J. Balzar, Oshkosh, WI (US); Sarah L. Christoffel, Appleton, WI (US); Ann Marie Przepasniak, Appleton, WI (US); Marci E. Sojka, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 601 days.

(21) Appl. No.: 11/125,725

(22) Filed: May 9, 2005

(65) Prior Publication Data

US 2006/0251464 A1 Nov. 9, 2006

(51) Int. Cl.
*B43K 5/14* (2006.01)

(52) U.S. Cl. .................. 401/133; 401/132; 401/205

(58) Field of Classification Search .............. 401/132, 401/133, 205; 206/222; 604/3
See application file for complete search history.

(56) References Cited

U.S. PATENT DOCUMENTS

| | | | |
|---|---|---|---|
| 3,085,681 A | 4/1963 | Fazzari | |
| 3,565,738 A | 2/1971 | Kirkpatrick | |
| 3,722,174 A | 3/1973 | Bergevin et al. | |
| 3,783,089 A | 1/1974 | Hurst et al. | |
| 3,924,008 A | 12/1975 | Ford et al. | |
| 3,940,905 A | 3/1976 | Perry, III | |
| 3,958,750 A | 5/1976 | Prybeck | |
| 4,190,154 A | 2/1980 | Clark | |
| 4,337,862 A | 7/1982 | Suter | |
| 4,348,440 A | 9/1982 | Kriozere | |
| 4,545,180 A | 10/1985 | Chung et al. | |
| 4,603,069 A | 7/1986 | Haq et al. | |
| 4,638,913 A | 1/1987 | Howe, Jr. | |
| 4,657,802 A | 4/1987 | Morman | |

(Continued)

FOREIGN PATENT DOCUMENTS

DE 1 264 317 B 3/1968

(Continued)

OTHER PUBLICATIONS

Miller, Edward E., "A Simple Test for Dispersion of Wet Chop Fiberglass in Water," *TAPPI Proceedings—1996 Nonwovens Conference*, pp. 71-85.

*Primary Examiner*—David J Walczak
(74) *Attorney, Agent, or Firm*—Denise L. Stoker; Randall W. Fieldhack

(57) ABSTRACT

A fluid-containing pouch is presented including a top layer having an outer surface; a bottom layer attached to the top layer and forming a cavity therebetween; an opening in the top layer allowing fluid communication between the cavity and the outer surface; a seal removably attached to the outer surface and sealing the opening; and a pull tab affixed to and overlying the seal. A cleaning device is also presented including a base layer; a wipe layer attached to the base layer to form an interior space therebetween, and; a pouch positioned within the interior space, the pouch having a top layer, a bottom layer attached to the top layer to form a cavity therebetween, an opening in one of the top and bottom layers, a seal affixed to the pouch and sealing the opening, and a pull tab affixed to and overlying the seal.

22 Claims, 3 Drawing Sheets

U.S. PATENT DOCUMENTS

| | | | |
|---|---|---|---|
| 4,700,531 A | 10/1987 | Hsu et al. | |
| 4,705,197 A | 11/1987 | Gordon et al. | |
| 4,805,767 A | 2/1989 | Newman | |
| 4,840,270 A | 6/1989 | Caputo et al. | |
| 4,878,775 A * | 11/1989 | Norbury et al. | 401/132 |
| 4,889,234 A | 12/1989 | Sorensen et al. | |
| 4,890,744 A | 1/1990 | Lane, Jr. et al. | |
| 4,902,142 A | 2/1990 | Lammert et al. | |
| 4,910,292 A | 3/1990 | Blount | |
| 4,973,656 A | 11/1990 | Blount | |
| 4,978,232 A | 12/1990 | Dunton | |
| 5,012,930 A | 5/1991 | Hansen | |
| 5,022,526 A | 6/1991 | Crum | |
| 5,044,776 A | 9/1991 | Schramer et al. | |
| 5,059,035 A | 10/1991 | Kristensen | |
| 5,060,847 A | 10/1991 | Angus | |
| 5,090,832 A | 2/1992 | Rivera et al. | |
| 5,111,932 A * | 5/1992 | Campbell | 206/216 |
| 5,140,796 A | 8/1992 | Pope | |
| RE34,117 E | 10/1992 | Martin et al. | |
| 5,154,293 A | 10/1992 | Gould | |
| 5,161,687 A | 11/1992 | Kornell et al. | |
| 5,167,974 A | 12/1992 | Grindrod et al. | |
| 5,169,251 A | 12/1992 | Davis | |
| 5,221,143 A | 6/1993 | Peppiatt | |
| 5,273,514 A | 12/1993 | Kristensen | |
| 5,312,883 A | 5/1994 | Komatsu et al. | |
| 5,317,063 A | 5/1994 | Komatsu et al. | |
| 5,348,400 A | 9/1994 | Haiss et al. | |
| 5,382,400 A | 1/1995 | Pike et al. | |
| 5,417,040 A | 5/1995 | Davoren | |
| 5,443,154 A | 8/1995 | Hustad et al. | |
| 5,509,913 A | 4/1996 | Yeo | |
| 5,514,442 A | 5/1996 | Galda et al. | |
| 5,604,000 A | 2/1997 | May | |
| 5,616,201 A | 4/1997 | Finch et al. | |
| 5,674,010 A | 10/1997 | Dussich | |
| 5,695,868 A | 12/1997 | Mccormack | |
| 5,725,311 A | 3/1998 | Ponsi et al. | |
| 5,733,636 A | 3/1998 | May | |
| 5,770,528 A | 6/1998 | Mumick et al. | |
| 5,823,685 A | 10/1998 | Garlichs | |
| 5,824,380 A | 10/1998 | Hagen | |
| 5,843,056 A | 12/1998 | Good et al. | |
| 5,855,434 A | 1/1999 | Hagen | |
| 5,916,678 A | 6/1999 | Jackson et al. | |
| 5,937,615 A | 8/1999 | Forman | |
| 5,944,425 A | 8/1999 | Forman | |
| 5,948,710 A | 9/1999 | Pomplun et al. | |
| 5,952,251 A | 9/1999 | Jackson et al. | |
| 5,956,770 A | 9/1999 | Dennis | |
| 5,956,794 A | 9/1999 | Skiba et al. | |
| 5,971,971 A | 10/1999 | Saint-Ramon et al. | |
| 6,032,854 A | 3/2000 | Greer et al. | |
| 6,048,100 A | 4/2000 | Thrall et al. | |
| 6,113,271 A | 9/2000 | Scott et al. | |
| 6,126,009 A * | 10/2000 | Shiffler et al. | 206/494 |
| 6,171,292 B1 | 1/2001 | Osborn, III et al. | |
| 6,315,448 B1 | 11/2001 | Thrall | |
| 6,341,602 B1 * | 1/2002 | Fulcher | 126/263.07 |
| 6,350,057 B1 | 2/2002 | Forman | |
| 6,420,006 B1 | 7/2002 | Scott | |
| 6,428,867 B1 | 8/2002 | Scott et al. | |
| 6,508,602 B1 | 1/2003 | Gruenbacher et al. | |
| 6,547,468 B2 * | 4/2003 | Gruenbacher et al. | 401/133 |
| 6,588,961 B2 | 7/2003 | Lafosse-Marin et al. | |
| 6,589,622 B1 | 7/2003 | Scott | |
| 6,755,927 B2 | 6/2004 | Forman | |
| 2001/0010253 A1 | 8/2001 | Forman | |
| 2003/0039412 A1 | 2/2003 | Rodick | |
| 2003/0094466 A1 | 5/2003 | Duquet et al. | |
| 2004/0101214 A1 | 5/2004 | Feder | |
| 2004/0237235 A1 * | 12/2004 | Visioli et al. | 15/104.94 |
| 2005/0148959 A1 | 7/2005 | Przepasniak et al. | |
| 2005/0201812 A1 | 9/2005 | Wong et al. | |
| 2005/0244211 A1 | 11/2005 | Brunner et al. | |
| 2007/0048063 A1 | 3/2007 | Bauer et al. | |

FOREIGN PATENT DOCUMENTS

| | | |
|---|---|---|
| DE | 93 16 908 U1 | 4/1994 |
| DE | 298 01 621 U1 | 4/1998 |
| EP | 0 074 161 A2 | 3/1983 |
| EP | 0 175 451 A2 | 3/1986 |
| EP | 0 258 143 A1 | 3/1988 |
| EP | 0 279 632 A2 | 8/1988 |
| EP | 0 442 292 A1 | 8/1991 |
| EP | 0 453 105 A2 | 10/1991 |
| EP | 0 276 554 B1 | 3/1992 |
| EP | 0 517 566 B1 | 3/1995 |
| EP | 0 367 744 B1 | 6/1995 |
| EP | 0 658 480 A1 | 6/1995 |
| EP | 0 675 703 A1 | 10/1995 |
| EP | 0 829 433 A2 | 3/1998 |
| EP | 0 841 049 A1 | 5/1998 |
| EP | 0 990 511 A2 | 4/2000 |
| EP | 1 046 591 A2 | 10/2000 |
| EP | 1 198 512 A1 | 4/2002 |
| EP | 0 968 928 B1 | 3/2003 |
| EP | 1 375 380 A1 | 1/2004 |
| EP | 1 480 895 A1 | 12/2004 |
| EP | 1 217 914 B1 | 4/2005 |
| JP | 09-127874 A | 5/1997 |
| JP | 10-129745 A | 5/1998 |
| JP | 11-292164 A | 10/1999 |
| JP | 2000-168801 A | 6/2000 |
| JP | 2001-301807 A | 10/2001 |
| JP | 2004-189319 A | 7/2004 |
| NL | 1021437 C1 | 11/2003 |
| WO | WO 79/00590 A1 | 8/1979 |
| WO | WO 93/08982 A2 | 5/1993 |
| WO | WO 95/28331 A1 | 10/1995 |
| WO | WO 99/05045 A1 | 2/1999 |
| WO | WO 99/46182 A2 | 9/1999 |
| WO | WO 01/26499 A1 | 4/2001 |
| WO | WO 02/30251 A2 | 4/2002 |
| WO | WO 03/000106 A1 | 1/2003 |
| WO | WO 03/059776 A1 | 7/2003 |
| WO | WO 2006/121598 A1 | 11/2006 |
| WO | WO 2007/027277 A1 | 3/2007 |

* cited by examiner

DEVICE WITH PULL TAB ACTIVATION

BACKGROUND

This invention pertains to cleaning, absorbent, and application devices, and containers for liquids.

Cleaning devices and other similar devices that include a fluid container commonly include a bladder. Such bladders are designed to burst along a frangible seam or portion when pressure is applied to the device and therefore the bladder. Such devices are not selective and burst under sufficient pressure, whether that pressure is applied intentionally by a user, or that pressure is applied unintentionally during handling, shipping, or storage.

SUMMARY

Cleaning devices and other similar devices including bladders that contain fluids suffer from the problem of premature bursting of such bladders. The disclosure herein solves this problem by providing a cleaning device containing a soft flexible pouch of fluid. The flexible pouch is durable and is designed to not burst during normal handling.

A fluid-containing pouch is presented including a top layer having an outer surface; a bottom layer attached to the top layer and forming a cavity therebetween, an opening in the top layer allowing fluid communication between the cavity and the outer surface; a seal removably attached to the outer surface and sealing the opening; and a pull tab affixed to and overlying the seal.

A cleaning device is also presented including a base layer; a wipe layer attached to the base layer to form an interior space therebetween, and; a pouch positioned within the interior space, the pouch having a top layer, a bottom layer attached to the top layer to form a cavity therebetween, an opening in one of the top and bottom layers, a seal affixed to the pouch and sealing the opening, and a pull tab affixed to and overlying the seal.

A cleaning device is also presented including a base layer; a wipe layer attached to the base layer to form an internal space therebetween; and a pouch positioned within the internal space, the pouch having a top layer, a bottom layer attached to the top layer to form a cavity therebetween, an opening in one of the top and bottom layers, a seal affixed to the pouch and sealing the opening, and a means for unsealing the pouch.

Objects and advantages of the present invention will become apparent to those skilled in the art in view of the following description and the accompanying drawings.

DETAILED DESCRIPTION OF THE PREFERRED EMBODIMENTS

The aspects of the invention as described herein will be described for exemplary purposes as a cleaning device. The aspects of the invention, however, apply equally to other forms of products, including absorbent devices, application devices, and other cleaning devices including wipes, mops, mitts, and cleaning towels, among other devices.

The term "surface" and its plural generally refer herein to the outer or the topmost boundary of an object.

Described herein is a disposable cleaning device 10 for the removal of dirt, etc. from a surface. Such a cleaning device 10 allows a user to clean a surface.

Figure 1:
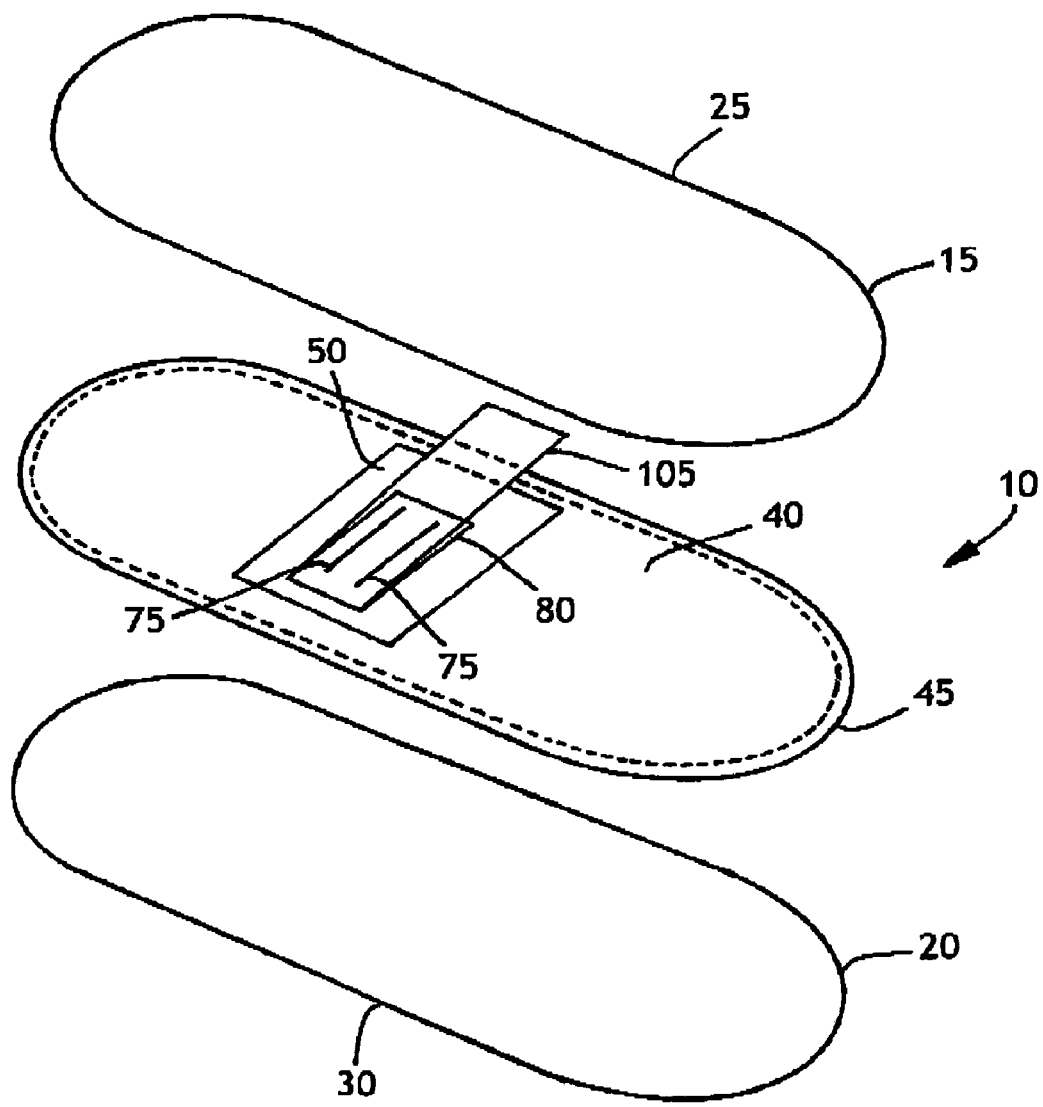
FIG. 1 is an exploded perspective view of an aspect of the present invention.

FIG. 1 illustrates an example of a cleaning device 10 as an aspect of the present invention. The device 10 includes a wipe layer 15 and a base layer 20. For purposes of illustration, and not for purposes of limitation, the cleaning device 10 is described as a pad.

The device 10 includes a wipe layer 15. The wipe layer 15 may be of any suitable shape, but is preferably generally planar and is further preferably generally rectangular or oblong. The wipe layer 15 has a perimetric edge 25 extending around the wipe layer 15. In one aspect of the present invention, the wipe layer 15 is generally the size of a human hand held flat on a surface. In another aspect of the present invention, the wipe layer 15 is generally the size of the four fingers of a human hand. In still another aspect of the present invention, the wipe layer 15 is generally the size of a human finger. The device 10 may be manufactured in any shape or of any dimensions, including as a pad may be sized to fit best in a child's hand, an adult hand, or on any cleaning implement. In general, the wipe layer 15 may be of any suitable size, with the size preferably selected to be suitable for the intended use of the cleaning device 10. In other aspects of the present invention, the device 10 can be manufactured into other shapes such as a mitt or square or round pads, etc.

The wipe layer 15 is an active layer, which performs the cleaning function. In alternate aspects of the present invention, any suitable coform, nonwoven, or woven material may be used. In one aspect of the present invention, the wipe layer 15 is an absorbent material. The wipe layer 15 may be a stretch-bonded laminate (SBL) with pre-stretched elastic filament and meltblown material with one ply of spunbond material on each outer surface and a basis weight of approximately 70 gsm, but any suitable absorbent material may be used. SBL and other composite nonwoven elastic webs are further described in U.S. Pat. No. 4,657,802 to Morman. In one aspect of the present invention, the wipe layer 15 includes a dry embossed 110 grams per square meter (gsm) coform laminate available from Kimberly-Clark Corporation.

In other aspects of the present invention, materials for the wipe layer 15 may include cotton, rayon, wood pulp, and polymeric substances such as nonwoven fabrics, foam sponges, and thermoplastics. The material may be formed of a nonwoven fabric that is made of interbonded thermoplastic fibers. The fibers may be formed from a variety of thermoplastic materials including polyolefins (e.g., polyethylene or polypropylene), polystyrene, and polyamides (e.g., nylon). In addition, thermoplastic polymers that are elastomeric may also be used as fibers, including polyurethanes and block copolymers. Blends of any of these materials may be used to form the fibers. The fibers may include additives (e.g., wax, pigments, stabilizers, and fillers) that are inserted as the fibers are fabricated to achieve one or more desired properties within the fibers. Some example additives include compatible surfactants that are added to the polymers to make the surface of the fibers more wettable, thereby improving the ability of the fiber structure to attract unwanted debris away from the skin. The amount of surfactant added to the fibers can be adjusted to control the surface wetting of the fabric formed from the fibers. Examples of suitable surfactants include sodium dioctyl sulfosuccinate and alkyl phenoxy ethanol.

Material used in making the wipe layer 15 may be capable of capturing and/or storing substances within the material. Such material may store and/or capture debris, cleansers, lubricants, spermicidal agents, and medications, among other materials, before or while using the device 10. Examples of such materials include spunbond, spunlace, bonded carded web, and apertured film materials. In one aspect of the present invention, the material is an apertured film that is formed of a polyolefin that may be combined with a nonwoven fabric. In other aspects of the present invention, the material of the wipe layer 15 may be a laminate of like, similar, or different tissue, nonwoven, woven, or film materials, or of any other materials described herein.

When a nonwoven fabric is used, the basis weight of the nonwoven fabric may vary depending on the properties that are desired within the device 10. As an example, the basis weight for the nonwoven fabric may be as low as 10 gsm and as high as 300 gsm. Such nonwoven materials may include a textured surface. Examples of such nonwoven textured materials include rush transfer materials, flocked materials, wire-form nonwovens, and thermal point unbonded materials, among others.

In one aspect of the present invention, the wipe layer 15 may be used dry to absorb liquids from a surface. In another aspect of the present invention, the wipe layer 15 may be dampened by a user with water or another substance to aid cleaning with the cleaning device 10.

The cleaning device 10 also includes a base layer 20. The base layer 20 is preferably of the same general size and shape of the wipe layer 15, although the size and/or shape of the base layer 20 may be selected to be different from the size and/or shape of the wipe layer 15 based on the intended use of the cleaning device 10. The base layer 20 has a perimetric edge 30 extending around the perimeter of the base layer 20.

The base layer 20 may be a backing layer. The base layer 20 may be manufactured from any suitable nonwoven, woven, or paper tissue material. In one aspect of the present invention, the base layer 20 is an absorbent material. The base layer 20 may be SBL with pre-stretched filament and meltblown material with one ply of spunbond material on each outer surface and a basis weight of approximately 70 gsm, but any suitable absorbent material may be used. In one aspect of the present invention, the base layer 20 includes a dry embossed 100 gsm coform laminate available from Kimberly-Clark Corporation.

In an alternative aspect of the present invention, the base layer 20 is also an active layer and manufactured under any of the aspects of the present invention described above for the wipe layer 15. In the case of the base layer 20 as an active layer, the base layer 20 may be manufactured from a material similar to or different from that used for the wipe layer 15.

In an alternative aspect of the present invention, one or both of the wipe and base layers 15, 20 may be breathable to allow air to circulate through the device 10.

The wipe layer 15 is coupled to the base layer 20. One of the wipe and base layers 15, 20 is positioned to overlie the other of the wipe and base layers 15, 20, such that the perimetric edges 25, 30 of the wipe and base layers 15, 20 generally align. A portion of the perimetric edge 25 of the wipe layer 15 is attached to the perimetric edge 30 of the base layer 20 to form a seam 35 (see FIG. 3). The seam 35 formed may be at the perimetric edges 25, 30, or the seam 35 may be adjacent or inward from the perimetric edges 25, 30. The wipe and base layers 15, 20 may be attached by adhesive, ultrasonic bonding, heating, sewing, or by any other suitable method. In one aspect of the present invention, the wipe and base layers 15, 20 are attached using a block copolymer adhesive such as 34-5610 construction adhesive available from National Starch. The wipe and base layers 15, 20 may also be attached at locations in addition to or other than the perimetric edges 25, 30.

Returning to FIG. 1, coupling the wipe layer 15 to the base layer 20 forms the device 10 with an interior space 40.

The base layer 20 may include a liquid impermeable barrier layer 45 facing the interior space 40. In one aspect of the present invention, the material of the barrier layer 45 is a polyolefin-type material that can be heat sealed or ultrasonically sealed. In another aspect of the present invention, the material of the barrier layer 45 is a material such as BSTL, a breathable, stretchable, thermal laminate. BSTL and similar materials are described in U.S. Pat. No. 5,695,868 to McCormack et al. and U.S. Pat. No. 5,843,056 to Good et al. In yet another aspect of the present invention, the material of the barrier layer 45 may be SBL as described above, or may be any other suitable material, particularly those described above with reference to the wipe layer 15. Because the base layer 20 is the layer most likely to contact a user's hand, the barrier layer 45 acts to keep the base layer 20 and thus the user's hand dry. The barrier layer 45 may also be positioned adjacent a portion of the wipe layer 15 to occlude a portion of the wipe layer 15 from fluid contact, allowing that portion of the wipe layer 15 to remain dry. Separate barrier layers 45 may also be positioned adjacent the base layer 20 and adjacent the wipe layer 15.

By virtues of the design and materials chosen for the device 10, the device 10 is preferably designed to be disposable. In this case, disposable means that the device 10 is disposed of, rather than cleaned, after use.

In an alternative aspect of the present invention, the wipe layer 15 and the base layer 20 are two portions of the same piece of material. One of the wipe layer 15 and the base layer 20 is folded over the other of the wipe layer 15 and the base layer 20, and a portion of the perimetric edges 25, 30 are coupled by any means described herein to form the device 10.

Figure 2:
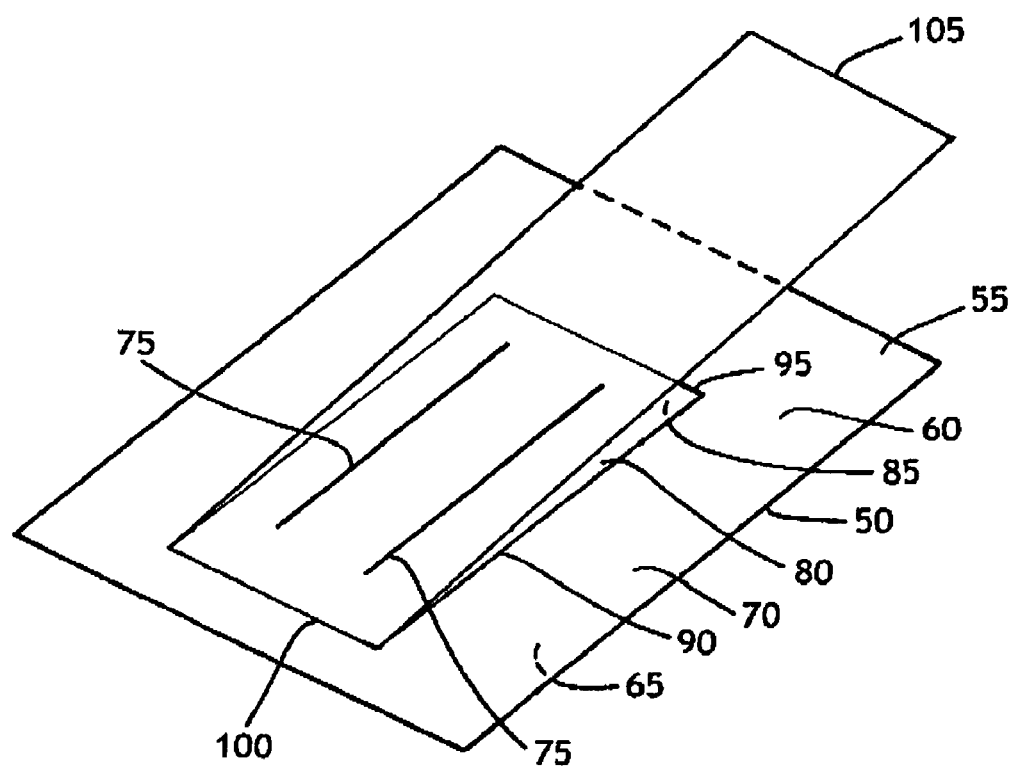
FIG. 2 is a schematic perspective view of an aspect of the pouch of FIG. 1.

As best shown in FIG. 2, the cleaning device 10 further includes a fluid-containing pouch 50. The pouch includes a top layer 55 having an outer surface 60, and a bottom layer 65 attached to the top layer 55. The top and bottom layers 55, 65 are attached such that they form and enclose a cavity 70. The top and bottom layers 55, 65 may attached by thermal bonding, although any suitable attachment method may be used. The cavity 70 may be sealed such that it contains a fluid. The pouch 50 may be rectangular, square, circular, oblong, or any other suitable size or shape.

The top layer 55 includes an opening 75 allowing fluid communication between the cavity 70 and the outer surface 60. The opening 75 may be one or more slits as shown in FIG. 1. In another aspect of the present invention, the opening 75 may be one or more holes, apertures, pin apertures, frangible portions, or may be of any suitable shape or size. The openings 75 may also be non-uniform in size or length.

The pouch 50 also includes a seal 80 that is removably attached to the outer surface 60 of the pouch 50. The seal 80 includes an adherent surface 85 and a free surface 90. The seal 80 also includes an attachment end 95 and a removal end 100. The adherent surface 85 of the seal 80 is affixed to the outer surface 60 such that the seal 80 blocks and thereby seals the opening 75. The seal 80 may be made from 2 mil polyethylene film available from Bemis Company, Inc., although any suitable material may be used. The seal 80 may be affixed to the outer surface 60 using an adhesive such as a pressure-sensitive acrylic adhesive or a frangible sealant poly available from Bemis Company, Inc.

In other aspects of the present invention, the adhesive used to attach the seal 80 to the pouch 50 may be EVA, polyolefins, reactive epoxies, starches, styrenic block copolymers (SBC), natural rubber, polybutylene, acrylics, polyurethanes, epoxies, polyesters, polyamides, silicones, and hot melt adhesives including EVA, SBC, and amorphous poly-alpha-olefin (APAO), with the use of APAO usually requiring the addition of a tackifier when used with polyethylene film. The adhesive may also be synthetic adhesives such as emulsion-based formulas (e.g., PVAc, EVA, rubber such as SBR and neoprene) or solution-based formulas (e.g., PVOH, Kymene, and Polyethylene oxide). The adhesive may also be a water-based adhesive such as those including either or both of natural and synthetic ingredients, such as polymers, thickeners, fillers, tackifiers, humectants, and wetting enhancers. The adhesive may be a natural adhesive such as starches (e.g., corn, tapioca, and wheat), dextrin, and animal glue.

In one aspect of the present invention, such adhesive is applied only to the portion of the seal 80 that contacts the outer surface 60. Sufficient pulling pressure applied to the seal 80, particularly at the removal end 100, will overcome the force of the adhesive, causing the adherent surface 85 to release from the outer surface 60, thereby unsealing the opening 75. In manufacture, the seal 80 may be placed on the pouch 50 before the pouch 50 is filled with fluid.

In one aspect of the present invention, the attachment end 95 of the seal 80 is affixed to the pouch 50, causing the seal 80 to remain affixed to the pouch 50 after the opening 75 is unsealed. In another aspect of the present invention, the attachment end 95 of the seal 80 is not affixed to the pouch 50, or is removably attached to the pouch 50, and the seal 80 can be completely removed from the pouch 50 when the opening 75 is unsealed.

The seal 80 also includes a pull tab 105 extending from the removal end 100 of the seal 80. The pull tab 105 may be an extension of and formed from the same material as the seal 80, or the pull tab 105 may be formed separately and then affixed to the seal 80. Pulling on the pull tab 105 thus pulls on the removal end 100 of the seal 80, causing the seal 80 to be removed from its position sealing the opening 75. In one aspect of the present invention, the pull tab 105 is folded back across the seal 80 to overlie the seal 80. In this position, pulling the pull tab 105 in a direction generally tangential to the outer surface 60 causes the pull tab 105 to pull on the removal end 100 of the seal 80. The seal 80 is thus peeled away from the pouch 50 as the adherent surface 85 detaches from the outer surface 60, thereby unsealing the opening 75. In one aspect of the present invention, and to ensure that the pull tab 105 remains in a position overlying the seal 80, the pull tab 105 may be removably attached to the free surface 90 of the seal 80 using adhesive or any other suitable attachment method. To be clear, the pull tab 105 and the seal 80 may be two regions of a single piece of material.

In one aspect of the present invention, the pull tab 105 may extend beyond the perimetric edges 25, 30 of the wipe and base layers 15, 20 (see FIGS. 1 and 3), thus making the pull tab 105 accessible to a user when the pouch 50 is positioned within the interior space 40. The pull tab 105 may thereby be removed from the interior space 40, or may remain at least partially within the interior space 40.

Figure 3:
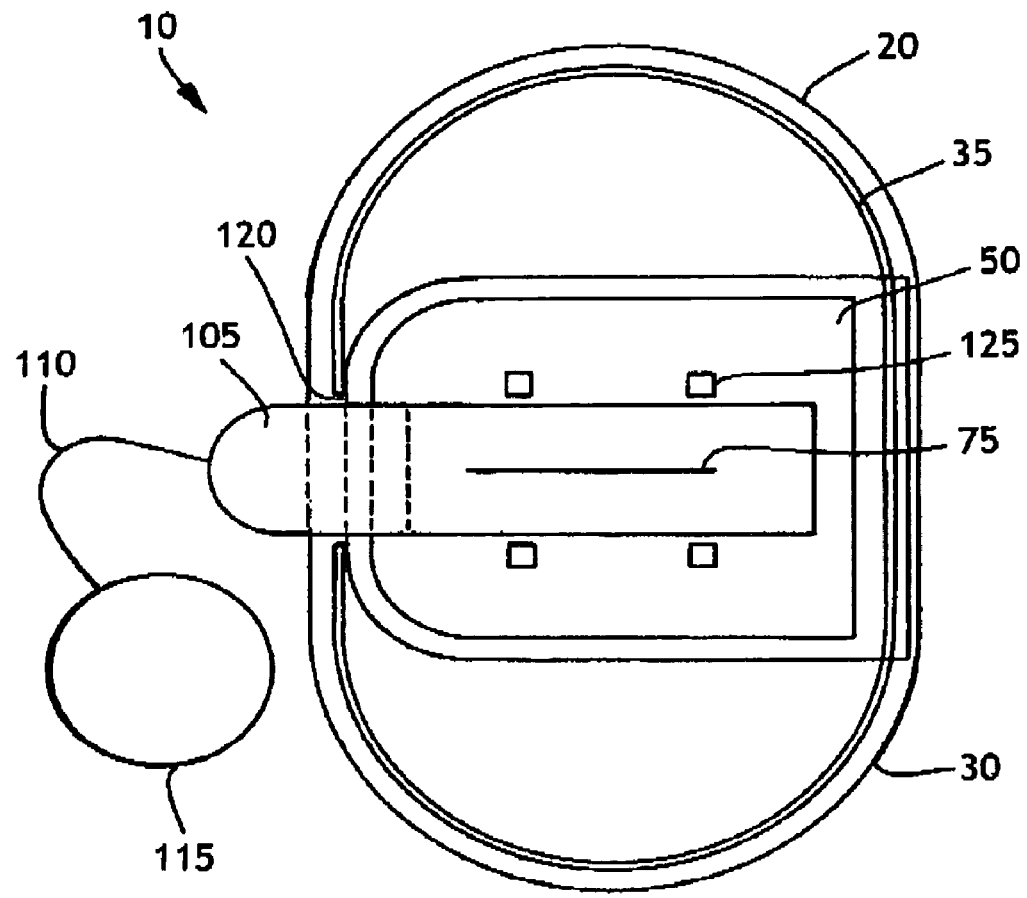
FIG. 3 is a cutaway plan view of an aspect of the present invention of FIG. 1.

In another aspect of the present invention best shown in FIG. 3, the pouch 50 may further include a pull string 110 affixed to the pull tab 105. In this case, the pull string 110 extends beyond the perimetric edges 25, 30 of the wipe and base layers 15, 20 and is accessible to a user. Pulling on the pull string 110 pulls on the pull tab 105, which thereby pulls on the seal 80 in the manner described above. The pull tab 105 may thereby be removed from the interior space 40, or may remain at least partially within the interior space 40. In still another aspect of the present invention, the pull string 110 may be affixed directly to the removal end 100 of the seal 80. In any of these aspects of the present invention, the pull tab 105 and/or the pull string 110 may be a string, ribbon, or pull cord. The pull tab 105 or pull string 110 may also include a tag 115 attached to the pull tab 105 or the pull string 110 to assist a user in pulling the pull tab 105 or the pull string 110. The device 10 may include a gap 120 in the seam 35 to allow the pull tab 105 or pull string 110 to pass through.

In various aspects of the present invention, a means for unsealing the pouch includes a pull tab 105 and a seal 80 combined as one piece of material; a pull tab 105 attached to and used in conjunction with a seal 80; a pull string 110 attached to and used in conjunction with a seal 80; a pull string 110 attached to a pull tab 105, which is combined with a seal 80 as one piece of material; and a pull string 110 attached to a pull tab 105, which is likewise attached to and used in conjunction with a seal 80 as one piece of material. The pull string 110 in each of these cases may be a string, ribbon, cord, or any other suitable material.

In one aspect of the present invention, the pouch 50 may also include one or more bonding points 125 at which the top layer 55 is affixed to the bottom layer 65. The bonding points 125 may be formed by any method described above for affixing the top layer 55 to the bottom layer 65 to form the pouch 50. The bonding points 125 act to inhibit the top layer 55 from moving relative to the bottom layer 65 when force is applied to the pull tab 105, the pull string 110, or the seal 80. In one aspect of the present invention, the bonding points 125 may be positioned within the cavity 70 and spaced apart from the edges of the pouch 50. Although described as points, in other aspects of the present invention the bonding points 125 may be lines, geometric shapes, or any other suitable shapes or sizes.

The pouch 50 is positioned within the interior space 40 of the device 10. The pouch cavity 70 may be sealed prior to being filled or partially filled with one or more fluids. The pouch 50 may be any size that fits within the interior space 40, with the size selected based on the fluid to be housed and the intended use of the device 10.

The pouch 50 can be sized to provide a level of over saturation that permits the fluid to soak through the wipe layer 15, permitting it to be absorbed by the intended surface. An example of this would be a stain removal cloth for carpet cleaning where it is desired to soak the stain.

The pouch 50 is made from a flexible, heat sealable material such as 2 mil polyethylene film available from Bemis Company, Inc. In other aspects of the present invention, the pouch 50 may be made from polyethylene, polypropylene, or other suitable thermoplastics. The material from which the pouch 50 is made should have no negative impact on or reaction with the fluid to be contained in the pouch 50. The materials used in the construction of the pouch 50 and the fill level of the fluid within the pouch 50 create a structure that is durable and flexible, and one that is not easily burst open during normal handling. In one aspect of the present invention, the pouch 50 is bonded to one of the wipe, base, or barrier layers 15, 20, 45.

As shown in FIGS. 1-3 for one aspect of the present invention, the pouch 50 is positioned within the device 10 to keep any edge of the pouch 50 away from the perimetric edges 25, 30 of the device 10. This is done to prevent the formation of any stiff edges in the device 10.

In another aspect of the present invention that is not shown, the device 10 may include a line of stitching, glue, or other suitable means to define a pocket within the interior space 40 to hold the pouch 50 in place.

In still another aspect of the present invention, the pouch 50 may include at least one opening 75 in each of the top and bottom layers 55, 60 of the pouch 50. In this aspect, each opening 75 would be sealed by a seal 80, each seal 80 having a pull tab 105 or pull string 110. Each opening 75 could be unsealed independently of the other. Each pull tab 105 or pull string 110 may be pulled independently, or the pull tabs 105 or pull strings 110 may be attached to each other to ensure coincident unsealing of the openings 75.

In an alternate aspect of the present invention that is not shown, the opening 75 may be replaced by a frangible portion that is ruptured upon removal of the seal 80. Such an aspect is particularly useful in the event that the fluid contents of the cavity 70 are reactive with or would act to weaken the adhesive used to attach the seal 80 to the pouch 50.

In another alternate aspect of the present invention that is not shown, the pouch 50 may include internal baffles or additional chambers to help control the release rate and distribution pattern of the fluid onto the wipe layer 15 upon removal of the seal 80.

In another aspect of the invention that is not shown, a distribution layer may be interposed between the pouch 50 and the wipe layer 15 to ensure fluid is distributed across the wipe layer 15. The distribution layer may be, for example, a surge material that wicks fluid to a substantial portion of the wipe layer 15.

In another aspect of the present invention, more than one pouch 50, or a pouch 50 including more than one cavity 70, may be used within the cleaning device 10. In this aspect, each pouch 50 or cavity 70 may contain the same fluid, allowing a user to unseal one or more pouches 50 to control the degree of saturation of the wipe layer 15. In a similar aspect of the present invention, the each pouch 50 or cavity 70 may contain a different fluid. The different fluids may be complementary, as in a cleaning fluid and a fragrance, or they may be reactive with each other to cause a desired action such as foaming, fizzing, a color change, warming, and cooling. In this aspect, each pouch 50 or cavity 70 would be sealed by a seal 80, each seal 80 having a pull tab 105 or pull string 110. Each pouch 50 or cavity 70 could be unsealed independently of the other. Each pull tab 105 or pull string 110 may be pulled independently, or the pull tabs 105 or pull strings 110 may be attached to each other to ensure coincident unsealing of the pouches 50 or cavities 70.

In another aspect of the present invention, a barrier layer 45 may be interposed between two pouches 50, allowing one pouch 50 to be in fluid communication with the wipe layer 15, and another pouch 50 to be in fluid communication with the base layer 20. As a result, one side of the device 10 could employ a pouch 50 with a cleansing fluid, while the other side of the device 10 could employ a pouch 50 with a rinsing fluid.

In still another aspect of the present invention, the fluid contained in the pouch 50 may react with a dry chemistry resident in either of the wipe or base layers 15, 20 to produce a sudsing, foaming, warming, cooling, or other chemical reaction. The dry chemistry may be, for example, a surfactant that is either applied to the wipe or base layers 15, 20, or that is included in the resin or binder fibers from which the wipe and base layers 15, 20 are manufactured.

In yet another aspect of the present invention, distribution of fluid into the wipe or base layers 15, 20 may be controlled by using materials with different wicking and other properties that will absorb and distribute the fluid in different patterns, rates, and manners.

The fluid contained in the cavity 70 of the pouch 50 may be any fluid suitable for the intended use of the device 10, including cleansing fluids for human/animal use and cleaning fluids for cleaning surfaces. The fluid may be any paste, gel, powder, oil, liquid, or any other appropriate medium. Example cleansing fluids include surfactants such as water-soluble polymers, polysorbates, glycerins, glycol-based surfactants, and/or silicone-based surfactants. The fluid may include other materials, such as water, salts, vinegars, humectants, scouring powders, thickening agents, and fragrances. A cleansing fluid may also include a moisturizer that helps to maintain a normal skin hydration level. A cleansing fluid may also include preservatives and other ingredients that do not disrupt the normal flora of the vaginal area (e.g., sorbic acid, citric acid, methyl paraben, and natural preservatives such as grapefruit extract). The fluid may include other materials that may be applied to an area of the body. Example materials include lubricants, deodorants, and other inactive or active ingredients (e.g., spermicidal agent or medication). In one aspect of the present invention, the fluid is a cleansing fluid that is primarily a water-based solution (90%+water content) with a surfactant, preservatives, pH neutralizers, and a thickening agent.

The fluid may be a cleaning solution such as FOUR PAWS Super Strength Stain and Odor Remover, which includes water, natural enzymes, and mild detergent (from Four Paws Products, Ltd., Hauppauge, N.Y.), or NATURE'S MIRACLE Stain & Odor Remover, which includes water, natural enzymes, isopropyl alcohol, and natural citrus scent (from Pets 'N People, Inc., Rolling Hills Estates, Calif.), or RESOLVE Carpet Spot & Stain Carpet Cleaner (from Reckitt Benckiser, Wayne, N.J.). The fluid may be a pet shampoo. The fluid may be a stain cleaner and stain guard such as SCOTCH-GARD Oxy Carpet Cleaner with Stain Protector that includes water, 2-butoxyethanol, hydrogen peroxide, and surfactants (from 3M Corporation, St. Paul, Minn.). In the case of using the cleaning device 10 to clean a fabric surface, the fluid may include a pet repellant such as SIMPLE SOLUTION Indoor/Outdoor Repellent for Dogs and Cats, which has as an active ingredient methyl nonyl ketone (from The Bramton Company, Dallas, Tex.).

The fluid may be an antimicrobial. Examples of suitable antimicrobials include quaternary ammonium compounds such as 3-trimethoxysilylpropyldimethyloctadecyl ammonium chloride (AEGIS); poly cationic chemicals such as biguanides (poly (hexamethylene) biguanide hydrochloride (PHMB) Arch Chemical), 2,4,4'-Trichloro-2'-hydroxyl-dipenylether (Tinosan, Ciba); diphenyl ether (bis-phenyl) derivatives known as either 2,4,4'-trichloro-2'hydroxy dipenyl ether or 5-chloro-2-(2, 4-dichlorophenoxyl) phenol; triclosan; silver; and copper. The fluid may be an allergen sequestrant that may be a charged or mixed charged particle or nanoparticle. Most allergy proteins are glycoproteins (proteins that contain covalently-bound oligosaccharides), so a negative charge may be better then predominance of positive charges on the particles, although mixed charges may be preferred. Clays or modified clays work in this respect. Examples of suitable allergen sequestrants include plant lectins with an affinity for N-acetylgalactosamine such as jacalin, peanut, and soybean, where the lectins both bind allergens and are bound to the web, thus removing allergens from a surface. The fluid may also include a fragrance. The fluid may also include a pheromone to either attract or repel an animal. The fluid may also be shoe polish, a carpet cleaning solution, a stain removal fluid, kitchen floor and counter top cleaners, etc.

In use, a user pulls the pull tab 105 or the pull string 110 to unseal the opening 75 in the outer surface 60 of the pouch 50 as shown in FIG. 3. In one aspect of the present invention, as the pull tab 105 or pull string 110 is pulled, the seal 80 and the pull tab 105 or the pull string 110 are extracted from the interior space 40.

EXAMPLE

In an example of an aspect of the present invention, a cleaning device 10 was manufactured. The wipe layer 15 was formed from a dry embossed 110 grams per square meter (gsm) coform laminate available from Kimberly-Clark Corporation. The base layer 20 was formed from a dry embossed 100 gsm coform laminate available from Kimberly-Clark Corporation. The wipe layer 15 was coupled to the base layer 20 by sewing. The pouch 50 was positioned within the interior space 40 and was formed from 2 mil polyethylene film available from Bemis Company, Inc. The pull tab 105 was formed from 2 mil polyethylene film available from Bemis Company, Inc. The fluid included within the cavity 70 of the pouch 50 was distilled water. An adhesive was applied between the outer face 60 and the pull tab 105. The completed device 10 was subjected to various manual manipulations consistent with shipping and handling without rupturing the pouch 50. Finally, the pull tab 105 was pulled, thereby unsealing the pouch 50 and resulting in the wipe layer 15 becoming wet from the fluid contents of the pouch 50.

Embodiments of the invention have been described with reference to various specific and illustrative aspects and techniques. However, it should be understood that many variations and modifications may be made while remaining within the spirit and scope.

Accordingly, this is intended to embrace all such alternatives, modifications and variations that fall within the spirit and scope of the appended claims.

We claim:

1. A cleaning device comprising:
   a base layer;
   a wipe layer attached to the base layer to form an interior space therebetween, wherein the wipe layer comprises an absorbent material and;
   a pouch positioned within the interior space, the pouch having a top layer, a bottom layer attached to the top layer to form a cavity therebetween, an opening in one of the top and bottom layers, a seal affixed to the pouch and sealing the opening, and a pull tab affixed to and overlying the seal, wherein the seal is separate from the pouch top layer and the pouch bottom layer.

2. The device of claim 1, further comprising a barrier layer attached to the base layer.

3. The device of claim 1, further comprising a barrier layer positioned between the pouch and the wipe layer.

4. The device of claim 1, wherein the pouch is attached to at least one of the base layer, a barrier layer, and the wipe layer.

5. The device of claim 1, wherein the wipe layer is attached to the base layer by ultrasonic bonding.

6. The device of claim 1, wherein the wipe layer is absorbent.

7. The device of claim 1, wherein the opening is a slit.

8. The device of claim 1, wherein the pull tab is an extension of the seal.

9. The device of claim 1, wherein the base layer has an edge, and wherein the pull tab extends beyond the edge.

10. The device of claim 1, wherein the seal has an attachment end, and wherein the attachment end is affixed to the pouch.

11. The device of claim 1, wherein the seal is removably affixed to the pouch using adhesive.

12. The device of claim 1, wherein the seal has a removal end, and wherein the pull tab is affixed to the seal at the removal end.

13. The device of claim 1, wherein the seal has an adherent surface removably attached to the pouch, and wherein the seal has a free surface opposite the adherent surface.

14. The device of claim 13, wherein the pull tab is removably attached to the free surface.

15. The device of claim 14, wherein the pull tab is removably attached to the free surface using adhesive.

16. The device of claim 1, wherein the pouch comprises a bonding point affixing the top layer to the bottom layer.

17. The device of claim 1, wherein the wipe layer and the base layer are two portions of the same piece of material.

18. The device of claim 1, further comprising a second pouch positioned within the interior space.

19. The device of claim 18, further comprising a second seal removably attached to the second pouch.

20. The device of claim 19, further comprising a second pull tab attached to the second seal, wherein the two pull tabs are coupled.

21. A cleaning device comprising: a base layer; a wipe layer attached to the base layer to form an internal space therebetween, and; a pouch positioned within the internal space, the pouch having a top layer,
   a bottom layer attached to the top layer to form a cavity therebetween,
   an opening in one of the top and bottom layers, a seal affixed to the pouch and sealing the opening, wherein the seal is separate from the top layer and the bottom layer, and a means for unsealing the pouch that extends from between the wipe layer and the base layer.

22. The device of claim 1, wherein the pull tab extends from between the wipe layer and the base layer.

* * * * *

UNITED STATES PATENT AND TRADEMARK OFFICE
CERTIFICATE OF CORRECTION

| | |
|---|---|
| PATENT NO. | : 7,651,290 B2 |
| APPLICATION NO. | : 11/125725 |
| DATED | : January 26, 2010 |
| INVENTOR(S) | : Bauer et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 825 days.

Signed and Sealed this

Twenty-third Day of November, 2010

David J. Kappos
*Director of the United States Patent and Trademark Office*